United States Patent
Seki et al.

[11] Patent Number: 6,164,787
[45] Date of Patent: Dec. 26, 2000

[54] CIRCADIAN CLOCK SEAT

[76] Inventors: Hoken S. Seki, 292 N. Sussex La., Lake Forest, Ill. 60045; Jefferson Perkins, 1356 Middleburg Rd., Naperville, Ill. 60540

[21] Appl. No.: 09/221,754

[22] Filed: Dec. 28, 1998

[51] Int. Cl.[7] .................................................. F21V 33/00
[52] U.S. Cl. .............................. 362/1; 362/127; 362/131; 607/88
[58] Field of Search .............................. 362/1, 127, 128, 362/138, 131, 470, 471, 511, 560, 562, 551; 606/2, 9, 10, 13; 607/88–94

[56] References Cited

U.S. PATENT DOCUMENTS

| | | | |
|---|---|---|---|
| 2,635,681 | 4/1953 | Hiltman et al. | 362/131 |
| 4,217,628 | 8/1980 | Windom | 362/75 |
| 5,944,748 | 8/1999 | Mager et al. | 607/88 |

OTHER PUBLICATIONS

Oren, D. and Terman, M., "Tweaking the Human Circadian Clock with Light", Science 279: 333–334 (Jan. 1998).
Campbell, S, and Murphy, P., "Extraocular Circadian Phototransduction in Humans", Science 279: 396–399 (Jan. 1998).
Hopkin, K., "Clock Setting", Scientific American, vol. 278, No. 4, pp. 20–22 (Apr. 1998).

Primary Examiner—Alan Cariaso
Assistant Examiner—Bertrand Zeade

[57] ABSTRACT

Apparatus for adjusting the biological clock of, e.g., an intercontinental or transcontinental airline traveler includes a luminaire disposed adjacent a front edge of a seat pan of a seat. The luminaire is coupled to or includes a light source; preferably the light source is disposed remotely from the luminaire and is coupled to the luminaire by a light guide. The luminaire may have a flexible reflecting element to increase light intensity on the backs of the traveler's knees. Using the luminaire to shine bright light on the backs of the knees of the traveler permits adjustment of the biological clock of the traveler in flight.

18 Claims, 2 Drawing Sheets

CIRCADIAN CLOCK SEAT

BACKGROUND OF THE INVENTION

Humans are largely diurnal organisms and have biological clocks that are, usually and at least roughly, set to the dark/light cycles caused by the rotation of the earth around its own axis. In premodern times, the time of day was kept as "solar" time; the end of each day, and the beginning of the next, were tied to when the sun came up and went down at that location on the earth. Twelve O'clock midnight in one location differed by a few seconds from twelve o'clock midnight a few miles away east or west. The change of the time as a function of change of longitude was not a problem before air travel became possible; with even the fastest premodern methods of travel, the traveler's biological clock easily adjusted to whatever time was extant at the location at which he was arriving.

It was only with the advent of intercontinental commercial aviation in the last half of the twentieth century that travel became so rapid that the body's biological clock could no longer easily adjust. "Jet lag" became a phenomenon. Conventionally, the intercontinental traveler is faced with two choices: attempt to function at the new location with a sleep deficit, usually at reduced efficiency; or spend one or two additional days resting and adjusting to the time of day at the new location. Then, at the terminus of the traveler's visit, jet lag is experienced in the other direction, and is dealt with in much the same way. This traditional coping mechanism is very wasteful of a traveler's time and is an impediment to productivity. To a somewhat lesser extent, the same situation is true for travel within a continent, depending on how far the trip extends, e.g., coast-to-coast travel within the U.S. mainland.

Recently, research has shown that the biological clock may be readjusted by shining a light on the popliteal region of the body, located at the back of a patient's knees. Oren, D. and Terman, M., "Tweaking the Human Circadian Clock with Light", Science 279: 333–334 (January 1998); Campbell, S, and Murphy, P., "Extraocular Circadian Phototransduction in Humans", Science 279: 396–399 (January 1998); Hopkin, K., "Clock Setting", Scientific American, vol. 278, no. 4, pp. 20–22 (April 1998). This finding was surprising because up until this time interaction with daylight conditions was believed to be only through the eyes. But because the back of the knee, or popliteal region, has many blood vessels relatively close to the surface, it can serve as a location at which light may interact with photoactive substances in the blood. A New York Times article reporting this finding (Jan. 16, 1998) suggested that travelers from New York to Paris could wear knee braces with light sources which would reset their biological clock as they slept during the flight. Still, this solution is cumbersome, adding to cabin clutter and requiring installation and removal at the beginning and end of the flight, and the inventors have come up with apparatus which will more easily accomplish the same objective.

SUMMARY OF THE INVENTION

According to one aspect of the invention, a seat, such as a conventional airline seat, is provided with a luminaire at a location adjacent the front edge of the seat pan. The luminaire is connected to a light source. Apparatus is provided to selectively actuate the light source to emit a bright light up and out onto the popliteal regions or the backs of the user's knees. Preferably, the light source is located remotely from the luminaire and is connected to the luminaire with a light guide such as one or more optical fibers. In this way, the luminaire can be made of flexible and even cushionable materials, and the light source, which can be any of several conventional types with hard parts and electrical power supply requirements, can be designed and specified without the constraints inherent in disposing such a light source under a body-receiving surface of a piece of upholstered furniture. The luminaire can be made of a light-transparent or translucent woven fabric, or can shine through a transparent or translucent material. Preferably, controls are provided such that the user can directly control the amount, intensity and length of time of the photoexposure.

A principal technical advantage inheres in the ability of the apparatus to adjust the user's circadian cycle without the user's eyes having to be open. For example, an airline passenger on a transcontinental or transoceanic flight may use the transit time to sleep, and have his or her circadian cycle adjusted by up to approximately three hours or more. This will dramatically reduce the effects of jetlag upon the passenger's arrival in a distant time zone, and concomitantly will reduce the amount of time needed by the traveler to adjust to the new time zone.

The present invention is primarily intended for use on passenger aircraft, but may be used on any article on which a person may be seated, whether in conjunction with other forms of transportation or otherwise, including seating in public and private locations on the ground.

BRIEF DESCRIPTION OF THE DRAWINGS

Further aspects of the invention and their advantages may be discerned from the following detailed description when read in conjunction with the drawings, in which like characters denote like parts and in which.

DETAILED DESCRIPTION OF PREFERRED EMBODIMENTS

Figure 1:
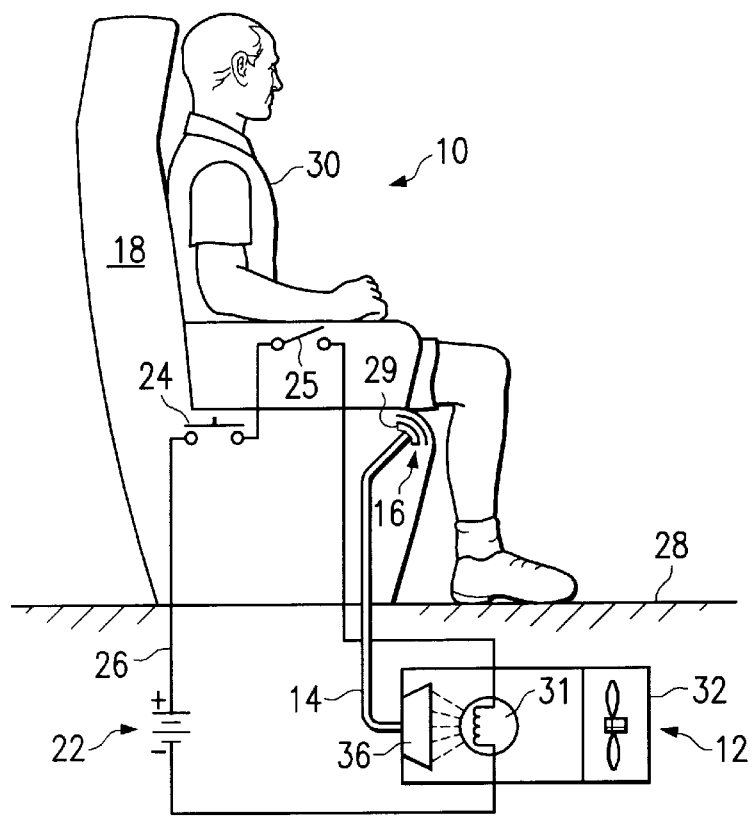
FIG. 1 is a part-elevational, part-schematic block diagram illustrating the principal components of the invention.

Referring first to FIG. 1, a circadian clock adjustment apparatus according to the invention is indicated generally at 10. The apparatus includes the following general components: a light source 12, which is adapted to generate a quantity of light sufficient to illuminate the popliteal regions with preferably at least 30,000 lux; a light conduit 14 that is connected to the light source 12 and which is capable of transmitting the required light energy with only small amounts of heat loss; and a luminaire 16 disposed in a seat 18 and connected to the light source 12 by the light conduit 14. A power supply 22, which for example can be a vehicular DC power supply, is connected to the light source 12 by one or more switches. In the illustrated embodiment, a pressure switch 24 has been placed in the power supply line 26 in series with a manually actuated switch 25. The pressure switch 24 is disposed in the seat below a top surface of the seat pan. The light source 12 is switched on by the combination of the user 30 sitting in the seat 18, thereby closing switch 24, and the user actuating manual switch 25. This obviates unwanted glare from a switched-on luminaire in an empty seat, which would be an irritant to persons sitting nearby. Alternatively or in addition, the switches can include one or more which are remotely and/or automatically controlled, as will be explained below.

Because in a preferred embodiment the light source 12 is positioned to be remote from the luminaire 16, the light source 12 can be any of several designs. In the embodiment shown in FIG. 1, which is a seat or chair in a long range aircraft, light source 12 may be disposed beneath a floor 28 of the passenger cabin. One power supply 22 is typically provided, such as the DC power of the aircraft. One light source 12 may be connected by several conduits 14 to respective seats 18. Because it preferably is not housed in the seat 18, the design constraints on maximum allowable dissipated heat and temperature are looser, as there is no insulative padding to heat up to uncomfortable levels or even catch fire. Remote positioning also simplifies problems which would be associated with an in-seat unit related to user comfort level, the ability of the unit to take a large and shifting load, and unit fragility. In one embodiment, the light source 12 is a halogen lamp 31 in a vented metal housing 32. A fan 34, which can be switched independently by a thermostat-activated switch (not shown), is used to prevent heat buildup. Light emitted by the lamp 31 is concentrated by a concentrator indicated schematically at 36 (which can be made up of a combination of reflectors, lenses and/or collimating prismatic sheets) to enter the light conduit 14.

The light conduit 14 is preferably a flexible tube or fiber optic bundle capable of receiving and delivering light energies of at least 30,000 lux. As implemented by a fiber optic bundle (such as one having about 4800 fibers), the light conduit 14 can be made of a material having an index of refraction with respect to air that is sufficiently high that total internal reflection along its length will result. Preferably the fiber optic bundle is encased in a flexible plastic tube. Optical fibers and bundles having this characteristic are well known in the art. A flexible conduit is preferred because a portion of the light conduit 14 must be installed in or adjoining the seat 18, and a yielding, flexible member will be more acceptable with respect to retaining adequate seat cushionability.

Several embodiments of the luminaire 16 are possible. In the embodiment illustrated in FIG. 2, the luminaire 16 includes a woven pad 29 of light-emitting fibers, with a light emitting area of at least 150 cm$^2$ per popliteal region. A single light emitting pad 29 of an elongated form can be used to illuminate both popliteal regions, for ease in connection and fabrication, or two separate spaced-apart pads can be used, one for each leg. In either design, provision should be made for variance in the human population on the lateral locations of the popliteal regions when sitting; some persons sit with their knees together, while others sit with them apart. By the use of such expedients as prismatic internal interfaces, the pad 29 can be so devised as to transmit light out of the pad toward the popliteal region 44 in such a way that the light is substantially orthogonal to the outer surface of the pad, reducing illumination in directions where it is neither wanted nor needed and increasing illumination efficiency.

Figure 2:
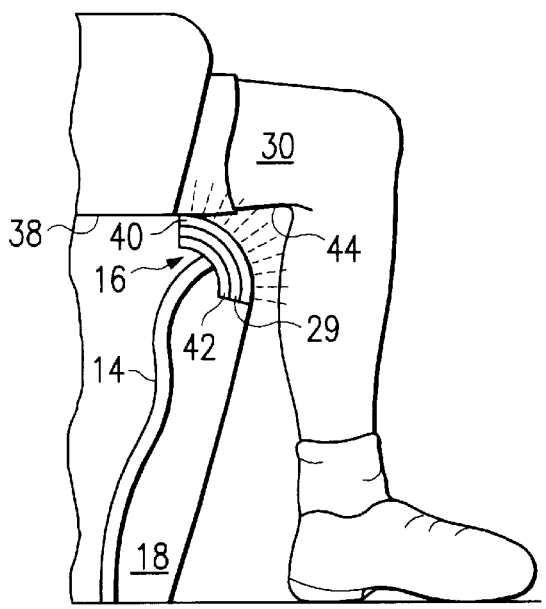
FIG. 2 is a sectional view of a circadian clock seat according to a first embodiment of the invention.

In FIG. 2, the pad 29 and related layers are stitched or otherwise affixed to the forward edge of a seat pan 38 of the seat 18. While in the illustrated embodiment the seat pan 38 is substantially horizontal, it is within the scope of this invention to form the seat pan as a portion of a reclining chair, such that the front edge of the seat pan is tipped upwardly with respect to the rear of the seat pan. Preferably, the seat should be so designed as to dispose the popliteal regions of the user adjacent to or forward from the front edge of the seat; this can be done by correctly positioning the seat back to provide a rear physical stop to the seat pan, and by elevating the seat pan above a floor, ground or footrest. Preferably, the chair or seat is so designed that the average user's femur will extend beyond the front edge of the seat pan, and that the average user's tibia will extend downward to a point below the forward edge of the seat pan. A protective layer or wear surface 40 is affixed on an outer surface of the woven pad 29. This protective layer should be transparent, yieldable, hypoallergenic, and reasonably comfortable to bare skin. Making the protective layer out of a nonporous material such as plastic makes it cleanable. The protective layer 40 must in any event be transparent to the light transmitted on light conduit 14. In an alternative embodiment, the pad 29 would be sufficiently wear- and water-resistant that it would in essence protect itself; in another embodiment, the layer 40 could be applied as a coating before or after the installation of the woven pad 29.

Preferably, the luminaire 16 includes a reflective layer or backing 42, positioned to reflect light upward back through pad 29 and layer 40, thus improving illumination efficiency and reducing heat generation. Similar to layers 29 and 40, the reflective layer 42 should be flexible. In one embodiment, layers 42, 29 and 40 are replaceable as a unit in those cases where the seat design life is greater than the useful life of the luminaire 16.

The depth or front-to-back extent of the woven-pad embodiment of the luminaire 16 should be sufficient to accommodate a large variation of passenger thigh length and a therefore similarly large variation in position of the popliteal regions 44, as will be described in more depth in conjunction with FIG. 4.

Figure 3:
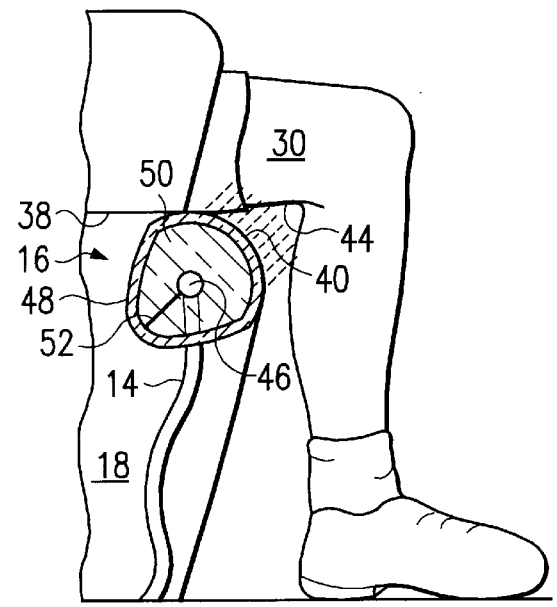
FIG. 3 is a sectional view of a circadian clock seat according to a second embodiment of the invention.

FIG. 3 shows an alternative embodiment of a luminaire 16 which uses the light-focusing characteristics of a cylindrical paraboloidal surface. In this embodiment, the light conduit terminates in a light emitter such as a rod 46 that is disposed side-to-side and horizontally in the seat 18. The luminaire 16 is once again disposed at a front edge of the seat pan 38, in proximity to the popliteal region 44 of a traveler.

The luminaire 16 includes a light-reflective surface 48 on or adjacent to its dorsal sidewall which conforms at least substantially to a cylindrical paraboloid with a long axis disposed in a transverse direction, or into the paper in FIG. 3. The rod 46 is located at the focus of this paraboloidal surface and at a remove from the upper/forward surface or ventral sidewall of the luminaire 16, which as in the last embodiment can be provided with a wear layer or coating 40. The rod 46 transmits light down its length from a central attachment point of the light conduit 14 to it. Along its length the outer surface of the rod 46 has light-intercepting and redirecting features (not shown), such as prismatic surfaces, which redirect the light outwardly. Some of the light from the rod 46 will be cast upwardly and forwardly without reflection from the mirror surface 48. The rest of the light from rod 46 will be reflected toward the popliteal region 44 in a substantially parallel, or slightly focused, manner.

One of the advantages of this embodiment is that the rod 46 does not have to be flexible or yieldable but instead can be a rigid structure that therefore has predictable optical behavior. But for the light emitting rod 46 to be rigid, it must be spaced away from the seat surface by a suitable yielding material, such that the user 30 will not be made uncomfortable by it. The interior of the luminaire 16 in this embodiment should be filled with a cushionable substance 50. One such substance is a gas such as nitrogen or air. This has a design drawback in that the wear surface 40 must be substantially gas impermeable, very tough, and proof against inadvertent or even intentional puncture by the users. Fluid and colloidal substances have the same problem. A solid interior filler 50 must be nonrigid, cushionable or yieldable and at the same time must be transparent. Certain silicone rubbers and other transparent elastomers have this characteristic. The substance 50 could be a foam or have air entrained into it, but this would decrease the directionality of the light coming out of the luminaire 16.

Where the substance 50 is a gas, liquid or a colloid, the light emitter 46 should be fixed in place by a support. As illustrated, the rod 46 is supported from a line below and aft of it on the reflecting surface 48 by a rigid cantilever support 52; a solid form of the transparent filler substance 50 would be sufficient to support the 46 without additional supporting structure. Alternatively, the support can take the form of one or more webs (not shown) which stretch across the entire diameter of the interior. In this embodiment, the luminaire 16 has dorsal and ventral sidewalls 48, 40 (the former reflective, the latter transparent or translucent) that together form a hermetically sealed body for containing the substance 50.

In a further embodiment (not shown), the emitter 46 may itself produce the light, as by fluorescence or other electrically actuated luminescence, and may be connected by suitable conductors to a source of electrical power.

Figure 4:
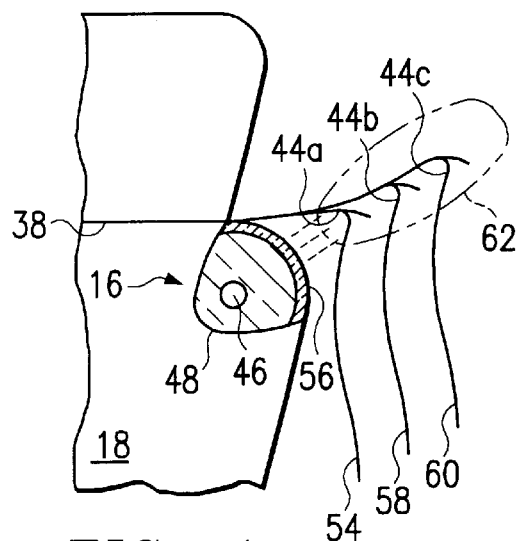
FIG. 4 is a detail of FIG. 3, schematically showing a locus of popliteal regions of different users.

FIG. 4 is a schematic illustration of the variance of user thigh length and the effect of that variation on the location of the popliteal region. A set of three profiles of the popliteal surface is shown. Profile 54 is for a relatively short person with a commensurately short femur and tibia. The popliteal region 44a is relatively close to the emitting rod 46 and is located at a relatively low altitude above the emitting rod 46. A profile 58 is shown for a person who is of medium height and therefore has a femur and tibia of medium length. The popliteal region 44b of such a person is displaced both outwardly and upwardly from popliteal region location 44a. The profile 60 is for relatively tall persons who will have relatively long femurs and relatively long tibiae, such that the popliteal region 44c is even further removed from the emitter rod 46 in both a vertical and a horizontal direction.

In order to accommodate persons of different heights, therefore, it is preferred that the luminaire 16 provide a substantially uniform illumination throughout a locus 62 in which the popliteal region is likely to occur. This can be accomplished, as shown, by a paraboloidal reflecting element, which will have a tendency to shine light outward in a beam of relatively constant intensity that does not disperse very much with distance. Even more preferably, the back reflector 48 can be shaped so as to produce a beam which slightly focuses the light such that there will be at least a predetermined amount of light intensity throughout locus 62.

Figure 5:
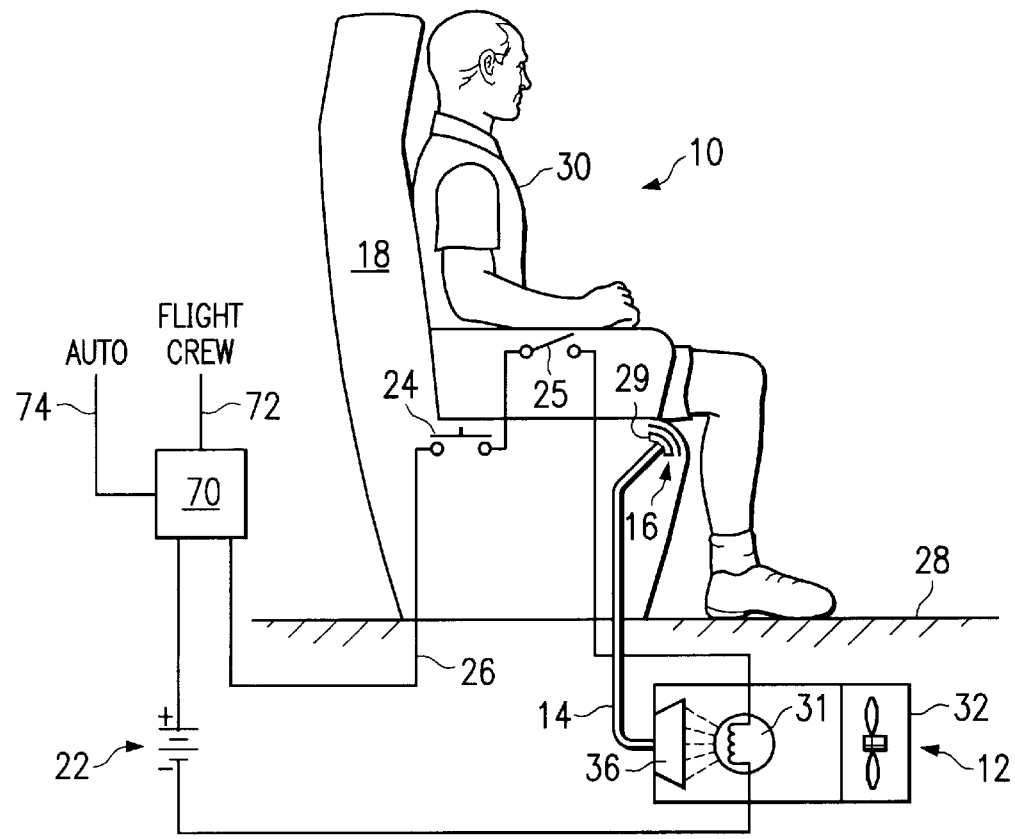
FIG. 5 is a schematic diagram similar to FIG. 1 but further illustrating controls by entities other than the user.

FIG. 5 illustrates an alternative embodiment of the invention. The schematically illustrated circuit is similar to that shown in FIG. 1, with the further provision of remote control of the apparatus by a person other than the user. A switch or relay 70 may be opened or closed according to a signal from one of the flight crew, received on line 72, or alternatively from the electronic logic associated with the aircraft, on signal line 74. The switch 70 may be actuated, for example, to be open when the aircraft in which the circuit is located is on a relatively short flight, when it is time to leave the aircraft, or in order to minimize power consumption by the aircraft. The relay 70 should also be linked to a sensor such as a thermistor (not shown) associated with the lamp source 31, so as to prevent overheating.

In operation, the user will need to bare his or her knees in any of several ways; a lap robe or the like could be provided for this purpose. In the preferred embodiment, the user will actuate pressure switch 24 automatically by sitting down in the seat, and will manually actuate switch 25 to turn on the light source 12. The user may, in one embodiment, select a period of time for which the light source is on, and in such an instance the switch 25 schematically illustrated in FIGS. 1 and 5 would include a timer element. Of course, as the light source is illuminating the popliteal regions, the user is free to do any other task which he or she could do from a sitting position, such as office work, reading or eating. The user can also sleep if he or she so chooses.

In summary, a method and apparatus for adjusting the circadian rhythm of travelers and in particular, air travelers, have been shown and described. However, while the present invention has been described in the above detailed description in conjunction with the appended drawings, the invention is not limited to these examples but only by the scope and spirit of the appended claims.

We claim:
1. Apparatus for reducing jetlag effects, comprising:
   a chair adaptable to receive a traveler and having a seat pan, the seat pan having a front edge, the depth of the seat pan preselected such that, when a traveler sits in the chair, the thighs of the traveler extend over the front edge of the seat pan, the seat pan being elevated such that the legs of the traveler will bend at the knee and extend downwardly below the plane of the seat pan;
   a luminaire mounted adjacent the front edge of the seat pan and adaptable to shine light upward and frontward, such that the popliteal regions of a traveler sitting in the chair are illuminated; and
   a source of light operatively connected to the luminaire to transmit light thereto,
   the intensity of the light preselected to bioactively change the biological clock of the traveler upon exposure of the popliteal regions of the traveler to light.

2. The apparatus of claim 1, wherein the chair has a back disposed adjacent a rear limit of the seat pan, the rear limit of the seat pan being opposed to the front edge of the seat pan.

3. The apparatus of claim 1, wherein the seat pan is elevated above the floor or ground.

4. The apparatus of claim 1, wherein the chair includes at least one footrest disposed at a location below the elevation of the seat pan.

5. A combination chair and therapeutic lamp for altering the biological clock of a person sitting in the chair, comprising:
   a seat pan having a front edge and a top surface, the seat pan being elevated and disposed such that the person's thighs will extend over the front edge and such that the person's calves will extend downwardly to a position below the elevation of the seat pan;
   a luminaire mounted in the chair adjacent the front edge of the seat pan and having a ventral sidewall and a dorsal sidewall, the ventral sidewall and the dorsal sidewall defining a luminaire interior, the ventral sidewall disposed frontward and upward of the dorsal sidewall and having at least a portion which is light-transparent such that light will shine through the sidewall from the interior upwardly and outwardly with respect to the front edge of the seat pan;

a light emitter disposed in the interior of the luminaire and adaptable to emit light of a predetermined intensity upwardly and outwardly through the transparent portion of the ventral sidewall to illuminate the backs of the person's knees; and means for making the light emitter emit the light.

6. The combination chair and therapeutic lamp of claim 5, wherein the interior of the luminaire is occupied by a gas.

7. The combination chair and therapeutic lamp of claim 6, wherein the gas is air.

8. The combination chair and therapeutic lamp of claim 6, wherein the light emitter is a light guide, the means making the light emitter emit the light comprising a light conduit coupling the light guide to a light source disposed exteriorly of the luminaire.

9. The combination chair and therapeutic lamp of claim 8, wherein the light source is disposed remotely from the luminaire.

10. The combination chair and therapeutic lamp of claim 9, wherein the chair is a seat in a vehicle, the light source being disposed in the vehicle but not in the chair.

11. The combination chair and therapeutic lamp of claim 10, wherein the vehicle is an airplane.

12. The combination chair and therapeutic lamp of claim 10, wherein the light source is disposed downwardly and rearwardly of the luminaire.

13. The combination chair and therapeutic lamp of claim 12, wherein the light source is actuated by electricity, the light source coupled to an electrical power source by a conductor.

14. The combination chair and therapeutic lamp of claim 13, wherein the conductor forms at least a portion of a conductive path between the electrical power source and the lamp, at least one switch in the conductive path permitting the selective energization of the lamp.

15. The combination chair and therapeutic lamp of claim 14, wherein the switch is disposed in the seat below the top surface of the seat pan and is actuated by the weight of the person as he or she sits down.

16. The combination chair and therapeutic lamp of claim 14, wherein the luminaire is a sealed chamber filled with a transparent, nonrigid substance and the ventral sidewall is yieldable, the ventral sidewall disposed proximate the front edge of the seat pan.

17. The combination chair and therapeutic lamp of claim 5, wherein the interior of the luminaire is filled with an elastically yieldable substance, the ventral sidewall of the luminaire forming at least a portion of the front edge of the seat pan and being flexible, the ventral surface presenting a cushionable surface to the thighs of the person; and means for disposing the lamp in the interior of the luminaire and spaced from the ventral sidewall even when the weight of the thighs of the person is compressing the ventral sidewall.

18. Apparatus for adjusting the biological clock of a person, comprising:

a seat having a seat pan, the seat pan having a front edge;

means for supporting the feet of the person;

the seat pan having a predetermined depth perpendicular to the front edge and a predetermined height, as measured from the means for supporting the feet of the person in a direction perpendicular to the depth;

a luminaire mounted in the seat to be adjacent the front edge of the seat pan and operable to illuminate any point within a popliteal region locus extending upwardly and frontwardly of the front edge of the seat pan with at least a predetermined light intensity;

a light source coupled to the luminaire to furnish light thereto; and a switch coupling the light source to a source of electrical power.

* * * * *